US00PP09796P

United States Patent [19]

Schumann et al.

[11] Patent Number: Plant 9,796

[45] Date of Patent: Feb. 4, 1997

[54] GERANIUM PLANT NAMED 'FLOSCALA'

[75] Inventors: Ingeborg Schumann, Albstadt; Angelika Utecht, Montabaur, both of Germany

[73] Assignee: Florfis AG, Binningen, Switzerland

[21] Appl. No.: 532,516

[22] Filed: Sep. 22, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Floscala, characterized by its white semi-double flowers, dark green foliage, low, but vigorous growth habit, and comparatively early flower response.

1 Drawing Sheet

The present invention comprises a new and distinct cultivar of geranium, botanically known as *Pelargonium zonale,* and hereinafter referred to by the cultivar name Floscala.

Floscala is a product of a planned breeding program which had the objective of creating new geranium cultivars which combine white flower color with intense green foliage and good chlorophyll stability.

Floscala was originated from a hybridization made by inventor Ingeborg Schumann in a controlled breeding program in Galdar, Gran Canaria, Spain in 1987. The female parent was a hybrid derived from crosses between Springtime Irene, a tetraploid line of Stadt Bern, and Bianca. Springtime Irene is a vigorously growing commercial variety with salmon pink semi-double flowers, medium green zoned foliage and vigorous growth. Stadt Bern is characterized by single orange-red flowers, dark green foliage with strong zonation and compact plant habit. Bianca has single white flowers in combination with large light to medium green leaves.

The male parent of Floscala was the cultivar Fisbal, disclosed in U.S. Plant Pat. No. 7,392, and characterized by white round semi-double flowers, medium green foliage and medium tall plant habit.

Floscala was discovered and selected as one flowering plant within the progeny of the stated cross by Ingeborg Schumann in 1988 in a controlled environment in Galdar, Gran Canaria, Spain.

The first act of asexual reproduction of Floscala was accomplished when vegetative cuttings were taken from the initial selection in June 1990 in a controlled environment in Galdar, Gran Canaria, Spain, by, or under the supervision of, inventor Angelika Utecht.

Horiticultural examination of plants grown from these cuttings initiated in May 1991, and continuing thereafter, has demonstrated that the combination of characteristics as herein disclosed for Floscala are firmly fixed and are retained through successive generations of asexual reproduction.

Floscala has not been observed under all possible environmental conditions. The phenotype may vary significantly with variations in environment such as temperature, light intensity and daylength, without however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Floscala, which, in combination, distinguish this geranium as a new and distinct cultivar:

1. Medium sized, semi-double flowers.
2. White flower color.
3. Dark green foliage with slight zonation.
4. Low and broad plant habit, medium vigor.
5. Relatively early flowering for a dark green cultivar.

Of the many commerical cultivars known to the present inventor, the most similar in comparison to Floscala are the parent variety Fisbal, the commercial cultivar Eclipse White, and the cultivar Fisalb, disclosed in a pending plant patent application.

Reference is made to attached Chart A which compares certain characteristics of Floscala to those same characteristics of Fisbal and Eclipse White.

In general comparison to Fisbal and Fisalb, Floscala has florets which consist of more petals, and darker green foliage.

In comparison to Eclipse White, Floscala grows less compact, its umbels are higher above the foliage, and its leaves are not quite so dark green as those of Eclipse White.

The accompanying color photographic drawing shows in top perspective view typical flower and foliage characteristics of Floscala, with colors being as true as possible with illustrations of this type.

In the following description, color references are made to The Royal Horticultural Society (RHS) Colour Chart. The color values were determined indoors from plants grown in a greenhouse in May 1994 in Hillscheid, Federal Republic of Germany.

Classification:

*Botanical.*—A hybrid of the species *Pelargonium zonale l'Hert.*

*Commercial.*—Zonal geranium, cv., Floscala.

Inflorescence.

Umbel:

*Shape.*—Flat, semi-spherical.

*Average diameter.*—110 mm.

*Average depth.*—50 mm.

*Peduncle length.*—120 mm.

*Peduncle color.*—Medium green, may turn red outdoors.

*Pedicel length.*—22 mm.

*Pedicel color.*—Medium green.

*Number of flowers per umbel.*—16.

Corolla:

*Average diameter.*—39 mm.

*Form.*—Semi-double.

*Number of petals.*—9–11.

*Number of petaloids.*—2–4.

*Color (general tonality from a distance of three meters).*—White; mature flowers may turn slightly pink outdoors.

*Color of upper petals.*—155 D.

*Color of lower petals.*—155 D.

*Markings of petals.*—Usually no markings; however, salmon-pink lines may occur on some of the petals.

*Color of lower surface of petals.*—155 A.

*Color of sepals.*—light to medium green.

*Number of sepals.*—5.

Bud:

*Shape.*—Elliptical to round.

*Color (adaxial).*—Medium green.

*Color (abaxial).*—Cream-colored, 155 A.

Reproductive organs:

*Androecium.*—2–4 fertile anthers, white filaments and orange pollen.

*Gynoecium.*—5–6 lobed stigma, style and stigma greenish white.

*Seed.*—No seed set observed.

Spring flowering response period: In Hillscheid, Germany, in 1994 plants and on average 1.1 umbels with at lease one flower opened 11 weeks after planting of unrooted cuttings.

outdoor flower production: The flower count in 1994 in Hillscheid, Germany indicated between 35 and 40 umbels per plant for May through August observation period.

Durability: Good shatter resistance, rain resistance average.

Plant

Foliage:

*Form.*—Kidney-shaped, open base.

*Margin.*—Bicrenated.

*Size of leaf.*—95 mm.

*Color of upper surface.*—Dark green, approximately 137 A.

*Color (zonation).*—Somewhat darker green, not always visible.

*Tolerance of botrytis.*—Average.

General appearance and form:

*Internode length.*—0.5–1.0 cm.

*Branching pattern.*—1.5 branches per week.

*Height of plants (foliage).*—20 cm, (in June, 16-week-old plants).

Ploidy: Tetraploid.

CHART A

| CHARACTERISTIC | FLOSCALA | FISBAL | ECLIPSE WHITE |
|---|---|---|---|
| No. of petals | 9–11 | 5–7 | 8–10 |
| Color of foliage | Dark green 137 A | Medium green, 137C–D | Dark green, 137A–147A |
| Size of flower (11-week-old plants) | 39 mm | 40 mm | 33 mm |
| Peduncles | 12 cm | 13 cm | 9.5 cm |
| Size of umbels | 11 cm | 10 cm | 8 cm |
| Height of plant | 20 cm | 24 cm | 18 cm |

It is claimed:

1. A new and distinct cultivar of geranium plant named Floscala, as illustrated and described.

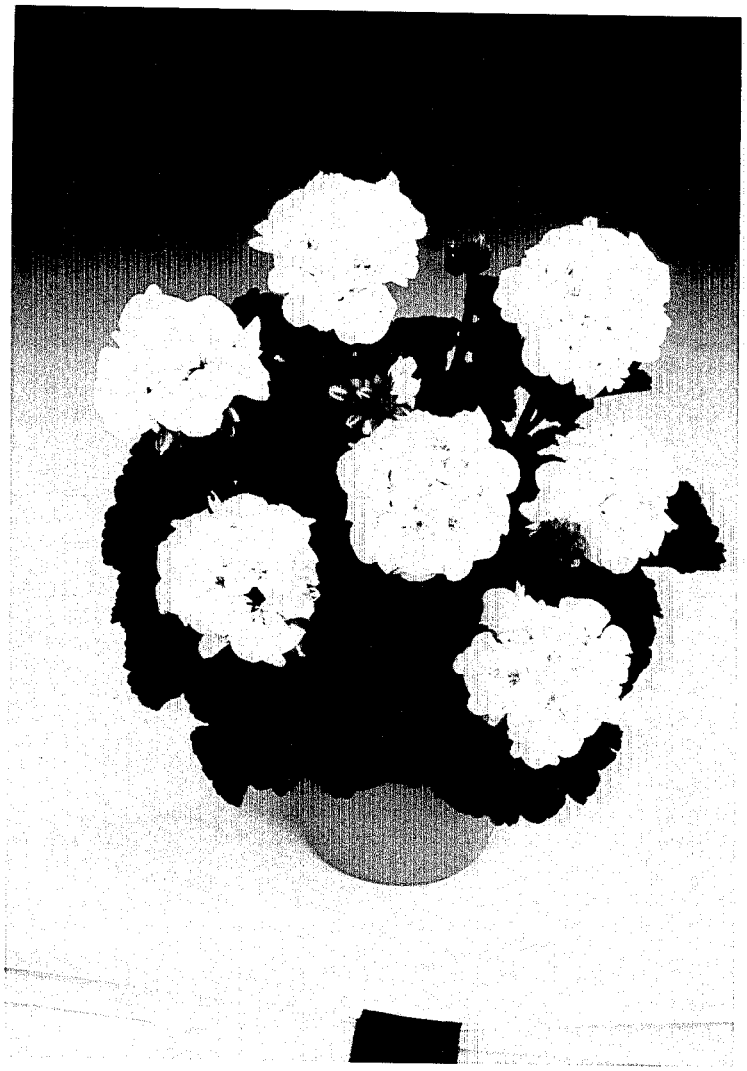

* * * * *